United States Patent [19]

Poler

[11] 4,435,050
[45] Mar. 6, 1984

[54] CONTACT LENS ASSEMBLY WITH HAPTIC AND METHOD FOR MAKING THE SAME

[76] Inventor: Stanley Poler, 78 E. Second St., New York, N.Y. 10003

[21] Appl. No.: 225,349

[22] Filed: Jan. 15, 1981

Related U.S. Application Data

[63] Continuation-in-part of Ser. No. 124,941, Feb. 26, 1980, Pat. No. 4,377,329.

[51] Int. Cl.$^3$ .............................. A61F 1/16; G02C 7/04
[52] U.S. Cl. ..................................... 351/160 R; 3/13; 351/177
[58] Field of Search ............... 351/160 H, 160 R, 161, 351/177; 3/13, 13 A

[56] References Cited

U.S. PATENT DOCUMENTS

| | | | |
|---|---|---|---|
| 3,594,074 | 7/1971 | Rosen | 351/160 R |
| 3,973,838 | 8/1976 | Page | 351/160 H |
| 4,080,709 | 3/1978 | Poler | 3/13 A |
| 4,095,878 | 6/1978 | Fanti | 351/161 |
| 4,122,556 | 10/1978 | Poler | 3/13 A |
| 4,126,904 | 11/1978 | Shepard | 351/160 R |
| 4,171,878 | 10/1979 | Kivaev et al. | 351/160 H |
| 4,268,133 | 5/1981 | Fischer et al. | 351/161 |

FOREIGN PATENT DOCUMENTS

| | | | |
|---|---|---|---|
| 908135 | 8/1945 | France | 351/160 R |
| 946877 | 12/1948 | France | 351/160 H |

*Primary Examiner*—John K. Corbin
*Assistant Examiner*—Scott J. Sugarman
*Attorney, Agent, or Firm*—Hopgood, Calimafde, Kalil, Blaustein & Judlowe

[57] ABSTRACT

The invention contemplates improved extraocular-lens structures for contact with the cornea of a human eye, to be worn in place of spectacles. The construction features a lens element of requisite prescription power but of diameter which substantially equals or only slightly exceeds the fully dilated pupil size of the wearer, and fenestrated haptic structure engaged to the lens extends radially outwardly and is so thin and axially compliant as to be self-conforming to the curvature of the cornea and to effectively adhere thereto, thus stabilizing the lens for retention of its position on the optical axis of the eye.

31 Claims, 19 Drawing Figures

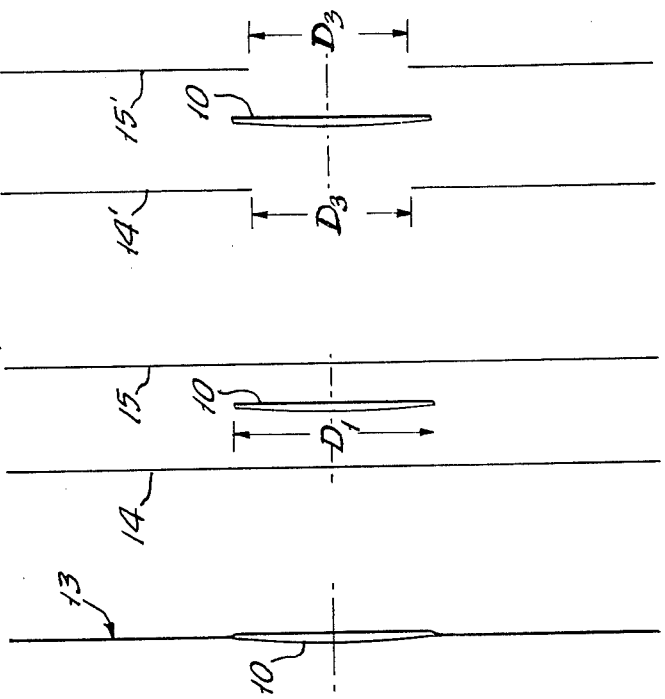
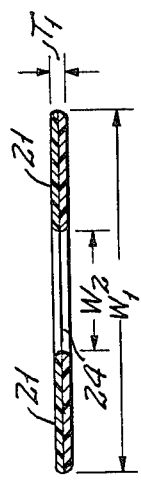
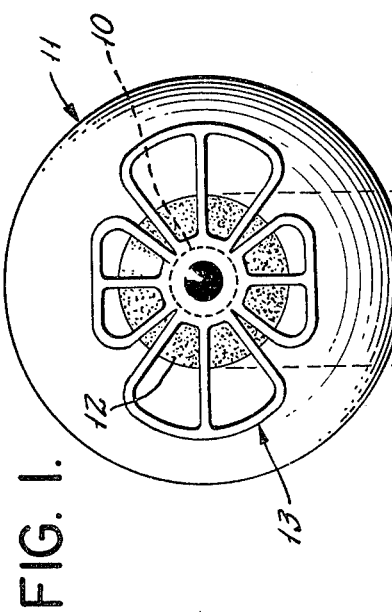
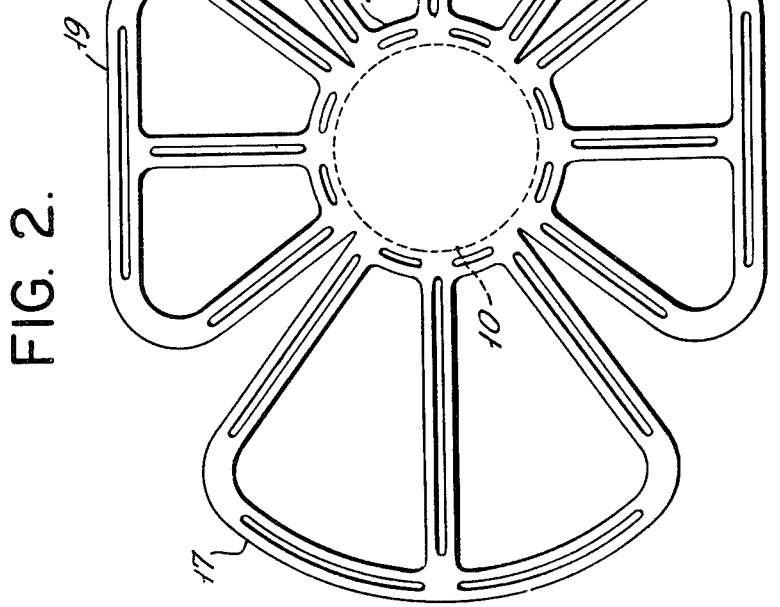

CONTACT LENS ASSEMBLY WITH HAPTIC AND METHOD FOR MAKING THE SAME

RELATED CASE

This application is a continuation-in-part of my co-pending application, Ser. No. 124,941, filed Feb. 26, 1980, now U.S. Pat. No. 4,377,329.

BACKGROUND OF THE INVENTION

This invention relates particularly to extraocular lens structures for contact application to the cornea, for wear in place of spectacles.

Conventional contact lenses, be they of the hard or soft variety, are circular, of 12 to 14 mm diameter, and thus cover a relatively large area, approximating the area defined by the perimeter of the iris. They are larger than optically necessary because the only light rays they need accommodate are those permitted by the pupil, and their relatively large area is a source of discomfort because fluid on the cornea is thereby precluded natural flow and circulation; as a consequence, the wearer of contact lenses must accustom himself to relatively frequent removal, cleaning and replacement of his lenses. But if the conventional contact lens were any smaller, it would be virtually incapable of manipulation by the wearer, and it would also be prone to move off-axis, over the corneal surface. Furthermore, liquid and gas-permeable plastics have recently been used, but lenses of such materials tend to build enzyme deposits and present difficulties in regard to cleaning and sterilization.

As far as I am aware, glass has been foreclosed as a contact-lens material, due to its high density and fragility compared to that of plastic materials. And the manufacture of contact lenses has involved plastic-molding techniques where prescription curvatures are derived from a molding cavity, or by lathe-cutting, i.e., they are not expressly not ground into the lens itself. And being circular, there is no way that astigmatism can be corrected through conventional contact lenses because there is no way of identifying orientation parameters of the astigmatism.

BRIEF STATEMENT OF THE INVENTION

It is an object to provide an improved extraocular or contact-lens construction.

It is a specific object to provide such a construction wherein the lens element itself may be of substantially smaller size, consistent essentially only with its optical requirements, and wherein haptic structure engaged to the lens element provides stabilized positioning for the lens element.

Another specific object is to meet the above objects with structure which is readily self-adapting to the curvature of the cornea.

It is also a specific object to provide structure meeting the above objects and permitting the employment of optical glass as the material of the lens element.

A further object is to provide a contact-lens construction inherently capable of supplying astigmatism correction for the wearer.

Still another object is to provide a contact-lens structure of the character indicated that can be cleaned and sterilized by boiling in water or by autoclaving.

It is a further specific object to provide protective structure in a contact lens whereby glass may be safely used as the optical element.

A general object is to meet the above objects with relatively simple structure which lends itself to quantity and precision manufacture, which inherently provides improved comfort to the wearer, and which involves substantially reduced demands for removal, cleaning and replacement.

The foregoing and the other objects and features of the invention are achieved in contact-lens constructions (a) wherein the lens element is of substantially reduced diameter (e.g., 5 to 8 mm), and is thus essentially only of the size required to serve a fully dilated pupil and (b) wherein fenestrated compliant haptic structure engages the lens element and adheres to the wet surface of the cornea for stabilized support of the lens element. The result is a much lighter-weight article, of less bulk than conventional contact lenses, and permitting the use of optical glass for the lens element.

DETAILED DESCRIPTION

The invention will be illustratively described in conjunction with the accompanying drawings, in which:

FIG. 1 is a simplified front-elevation view of a human eye to which contact-lens structure of the invention has been applied;

FIG. 2 is an enlarged view of the lens structure of FIG. 1 to show haptic detail;

FIG. 3 is a side-elevation view of the structure of FIG. 2;

FIG. 4 is a view similar to FIG. 3 but with the separate parts in exploded relation;

FIG. 5 is a view similar to FIG. 5 to show a modification;

FIG. 6 is a sectional view, taken at 6—6 of FIG. 2 and on a further-enlarged scale;

Figure 7:
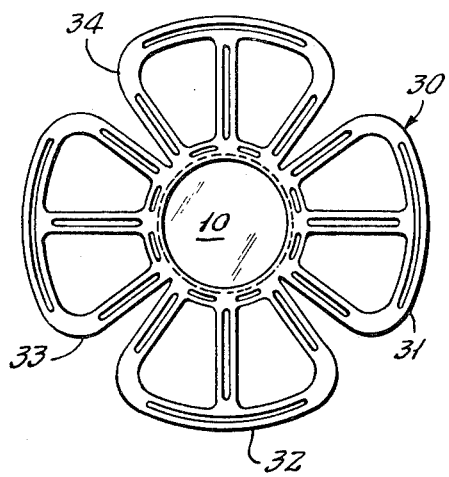
FIG. 7 is a view similar to FIG. 2, to show a modification.

In the form of FIGS. 1 to 4, the invention is shown in application to an extraocular or contact-lens assembly comprising a central lens element 10 which may be of molded plastic, but which is preferably of optically finished glass, ground to prescription curvature (e.g., plano-convex or meniscus) and of outside diameter $D_1$ which equals or slightly exceeds the diameter of the fully dilated pupil of a human eye. As is clear from FIG. 1, the diameter $D_1$ is very much less than the diameter $D_2$ of the iris 12 of the eye 11. Generally speaking, the diameter $D_1$, is in the range 5 to 8 mm, and the diameter $D_2$ is in the range of 12 to 14 mm, the latter being the diameter of a conventional contact lens.

Fixed to and centrally supporting the lens element 10 is a haptic 13 of much larger included area than the lens element 10. Haptic 13 comprises two thin sheets 14–15 of plastic material laminated to the front and back surfaces of lens element 10, and to each other in regions radially outside element 10; in these outer regions, haptic 13 is characterized by very substantial fenestration, meaning that the structure is primarily "open", for normal air or "breathing" exposure of the surface of the cornea. Such fenestration may be by photographically delineated milling, before or after lamination of the sheets 14–15 to each other, relying upon such chemical-etching, plasma and other milling techniques as are described for intraocular lens haptics, in my U.S. Pat. No. 4,080,709.

More specifically, each of the sheets of haptic 13 is seen to be of generally oval or elliptical outer contour and to comprise four radially outward foot formations, there being a first larger pair 16–17 on the major axis and a second shorter pair 18–19 on the minor axis. It is intended that these foot formations be very compliant in the axial direction, to render them self-conforming to the surface of the cornea. Each foot formation, taking formation 16 as typical, comprises angularly spaced outer legs 20 and a central leg 21 integrally connecting an inner hub portion 22 to an outer bridge portion 23; and intermediate their points of interconnection all these elemental areas are slotted, as at 24, to render them even more self-conforming to the surface of the cornea. The sheets 14–15 should be selected for autoclavability and may be of 1-mil or 0.5 mil material, suitably nylon, high-density polyethylene, Mylar*, Teflon*, polyethersulfone, polyester, sheet silicone, or H.E.M.A., meaning that in the elemental areas 20-21-22-23, the haptic is of thickness $T_1$ (FIG. 6) in the range of 1 to 2 mils; the width $W_1$ of each of these areas is typically in the order of 10 mils, and slot widths $W_2$ are in the order of 3 mils. The overall dimensions of the haptic blank may suitably be 16 mm. (major axis) by 12 mm (minor axis). Bonding of the plastic sheets 14–15 to each other may be by suitable ultrasonic, heating or cementing techniques, as applicable.
*Trademarks of the DuPont Company.

Prior to application to the cornea, the foot formations 16-17-18-19 are so axially weak ("floppy") as to be apparently useless as supports for the associated lens element 10. However, once the central lens-bearing region is placed over the pupil, the adjacent floppy haptic regions are drawn, by a self-wetting action akin to surface tension and/or capillary attraction (in the context of surface moisture on the cornea) to lie down on the cornea in conformance to locally adjacent curvature of the cornea. In addition to rendering the elemental areas 20-21-22-23 more compliant, the slotted regions (24) thereof achieve a pump-like coaction with surface liquid on the cornea, with the result that surface liquid is locally displaced and drawn into and through the slotted regions (24), and essentially all haptic area radially outside the lens element 10 has an affinity for the cornea region to which it has "attached" itself by self-wetting. Thus, the relatively narrow and slotted nature of areas 20-21-22-23 promotes displacement of surface liquid, with the attendant benefit of cleaning and lubricating action, particularly when blinking the eyelid over the installed structure. And the 1 to 2-mil haptic thickness encountered by a blinking eyelid is inconsequential, while the lens element remains sufficiently anchored in its installed eye-axis position, it being further noted that, as a result of using the indicated milling techniques, all edges of the haptic formations are smoothly rounded and therefore not a source of irritation. The anchoring effect is enhanced by providing a mildly roughened surface (as by etching) on the posterior side of the haptic areas 20-21-22-23, and the smoothness of eyelid action is enhanced by providing a smooth anterior surface of the haptic; the roughened surface will have been created prior to milling and will have a dull or matte appearance, and the smooth surface will be shiny, thus enabling ready identification of the front and back surfaces of the assembly.

In the form of FIGS. 1 to 4, the sheets 14–15 continuously and intimately cover the respective front and back surfaces of lens element 10. The selected plastic material of sheets 14–15 must therefore be for their transparency, and as noted previously, reliance is upon the lens element 10 for optical properties. Generally, it may be observed that use of plastic material for lens element 10 means an index of refraction substantially less than that of glass. Therefore, production of plastic lens elements 10 will mean greater curvature (shorter radii), and therefore greater lens thickness, than for a glass lens element 10 of the same diopter specification. In the case of the glass lens element 10, optical glasses are commercially available with various indices of refraction in the range 1.4 to 2.0, and I find that by grinding all lens elements 10 (as optically finished plano-convex elements), with the same single radius of curvature (e.g., 300-mm radius), a full range of prescribable diopter powers (at quarter-diopter increments, up to 10 diopters) is available merely by choice of the glass for its particular index of refraction; a similar single-radius approach in grinding negative-lens surfaces will also serve a wide range of diopter prescriptions, through appropriate selection of a particular glass for its index of refraction. Further, because glass elements 10 may be finished with prescribable grinding eccentricity, astigmatism correction can be provided, the lens element being oriented with its astigmatic-correction axis rotationally displaced to a prescribed angular orientation with respect to, say, the major axis 16–17 upon assembly to and lamination with the haptic parts 14–15; the exposed dull vs. shiny surfaces of the haptic, being recognizably exposed, enable the user to make sure that his installed lens (major axis horizontal, shiny side facing forward) will always be so installed in his eye as to avoid astigmatic ambiguity.

FIG. 5 illustrates a modification wherein each of the haptic sheets 14'–15' is formed with a central aperture of diameter $D_3$, to enable peripheral overlap with the rim of lens element 10; lamination of the sheets 14'–15' and their substantial fenestration radially outside lens element 10 is otherwise as described for FIGS. 1 to 4. The diameter $D_3$ is illustratively 4.5 to 5 mm, to allow such peripheral overlap to the radial extent of 0.5 to 0.75 mm, for the case of a 6-mm diameter $D_1$ of lens element 10.

FIG. 7 depicts an alternative construction, particularly suited to eyes for which no astigmatism is to be corrected. The only significant difference in FIG. 7 is that the outer perimeter of the haptic 30 thereof is generally circular. In other words, all foot formations 31-32-33-34 are alike, and preferably comprise slotted elemental hub, foot, and bridge areas corresponding to areas 20-21-22-23 of FIG. 2.

Figure 8:
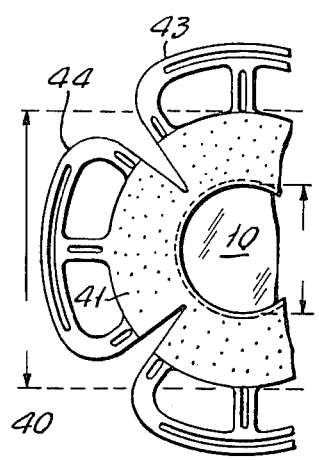
FIGS. 8 and 8A are fragmentary views, otherwise similar to FIGS. 7 and 2, respectively, to show another modification.
Figure 8A:
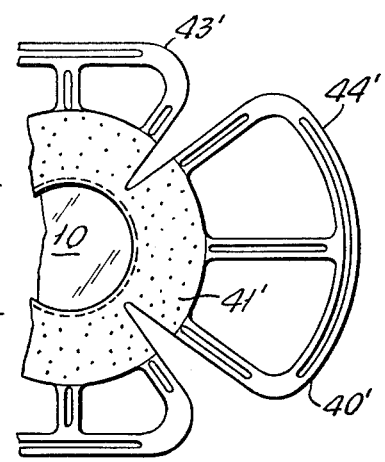

FIGS. 8 and 8A respectively illustrate circular and elliptically contoured embodiments of a modified version of the invention, particularly suited to the a-tonic iris, i.e., an eye having no iris or a damaged iris. One or both of the sheets which comprise the haptic 40 (40') is characterized by an opaque annular region 41 (41') extending from the lens-lapping inner diameter $D_3$ to an outer diameter $D_4$ to match the person's other-eye iris diameter. Foot formations 43–44 (43'–44') extend radially outward of the hub region of lens element retention, but the major open fenestration is radially outside the annulus 41 (41'), the "opaque" region 41 (41') being desirably foraminated with apertures of diameter preferably less than substantially 0.005 inch and at least as great as the thickness of region 41 (41'), to permit "breathing" action of the corneal surface covered thereby. Desirably, the "opaque" region is so finished as to color and design as to create the appearance of a normal iris in the afflicted eye.

Figures 9, 9A:
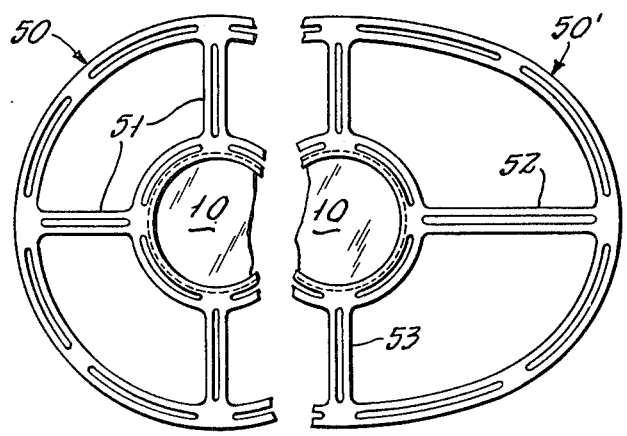
FIGS. 9 and 9A are similar to FIGS. 8 and 8A, to show further modification.

FIGS. 9 and 9A illustrate modification of the respective circular and elliptical embodiments of FIGS. 7 and 2, wherein the haptic 50 (50') is peripherally continuously a circle or an ellipse or oval. Slotting of elemental areas of haptics 50 (50') is again preferred, as described for FIG. 2. The floppy nature of the continuous periphery of both haptics 50 (50') enables continuous intimate attraction to the cornea surface in the manner described for FIGS. 1 to 4, and the plurality of axially compliant radial leg elements 51 (52–53) is preferably at least three, being shown as four, for both FIGS. 9 and 9A.

Figures 10, 10A:
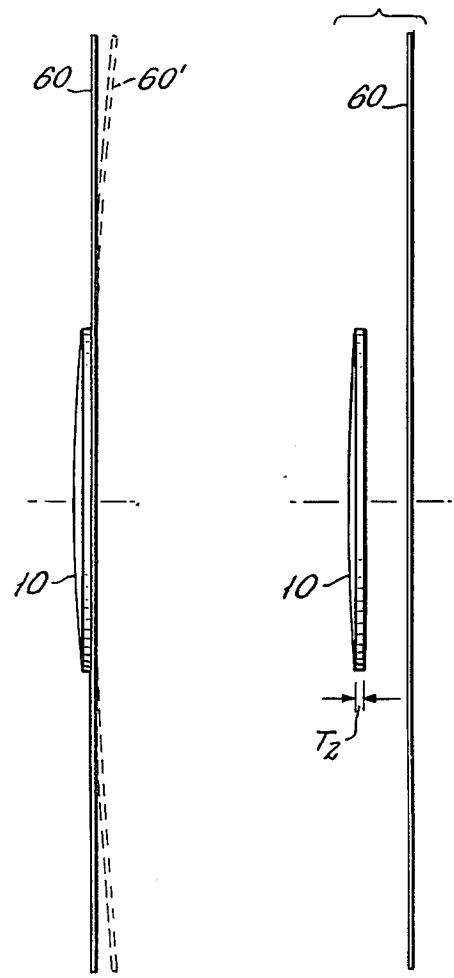
FIGS. 10 and 10A are views similar to FIGS. 3 and 4, respectively, to show further modification.

FIGS. 10 and 10A are directed to an all-glass embodiment of the invention wherein the lens element 10 is an optically finished element, shown as planoconvex and with a cylindrical rim of thickness $T_2$ in the range 1 to 3 mils, preferably substantially 2 mils. The flat posterior side of lens element 10 is mounted, as by fusing or by a suitable cement, to the central region of a sheet flass haptic 60 of thickness in the range 0.5 to 1.5 mils, preferably 1 mil. Fenestration is provided in the haptic region external to lens element 10, in the manner discussed above for the forms of FIGS. 2 and 7, 9 and 9A, as the case may be. The glass haptic 60 is thus substantially as floppy as its plastic counterpart, but it has the advantage of being less susceptible to bacteria-growth phenomena, and therefore less likely or less often to require removal for cleaning and sterilization; its ultimately flexed curvature in adaptation to the cornea is suggested by dashed lines 60.

Figure 11:
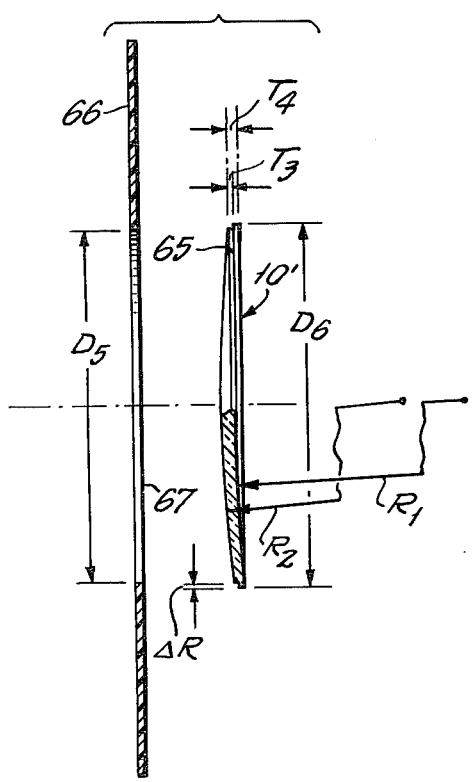
FIGS. 11 and 12 are views similar to FIG. 5 and 3, respectively, to show further modification.
Figure 12:
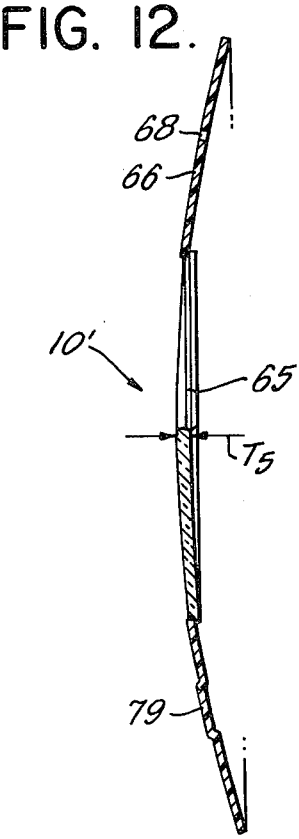

FIGS. 11 and 12 illustrate a further embodiment wherein the element 10' is a meniscus lens, having a concave axial-end surface of first spherical radius $R_1$ and a convex outer or opposite-end surface of second spherical radius $R_2$; in the illustration $R_1$ is shown to exceed $R_2$ and thus to define a positive meniscus lens 10', but the relation of $R_1$ to $R_2$ will be understood to be dictated by prescription appropriate to the optical correction needed by a particular eye. The circular periphery of lens element 10' is characterized by a rabbet formation 65, which may be etched, thus establishing a substantially cylindrical land of diameter $D_5$; the land terminates at a radially outward shoulder of outer diameter $D_6$, being the peripheral limit of the lens element. Typically, $D_6$ will be in the range 6.5 to 10 mm, and the etched shoulder height $\Delta R$ of the rabbet will be 0.1 to 0.25 mm, so that $D_5$ may be 6 mm or larger; at the same time, the axial depth $T_3$ of the rabbet may be about 0.05 mm, thus constituting a relatively harmless incursion upon the rim thickness $T_4$ of the lens element, $T_4$ being about 0.1 mm, and the maximum thickness $T_5$ (see FIG. 12) being approximately 0.5 mm and of course dependent on particular curvature radii $R_1$ and $R_2$. The curvature radii will generally be about 300 mm, respectively differing as much as 9 mm from each other, it being understood that the sense of the difference determines whether the lens element 10' is positive or negative.

The haptic 66 to which lens element 10' is assembled is shown flat in FIG. 11, since it is an annular blank cut, preferably by etching, from thin sheet material which may be glass or a suitable plastic. The central opening 67 of haptic 66 may be of the diameter $D_5$ of the rabbet land to which it is fitted; whether of glass or plastic, a suitable cement inert to body fluids may be employed to secure the assembled haptic (66) and lens (10') elements. Preferably, however, if haptic 66 is of glass, the diameter of opening 67 is selected for such slight interference with the diameter of the rabbet land that (1) upon heating to expand opening 67, the haptic will insertably receive the rabbet land to the point of circumferential abutment with the rabbet shoulder and (2) upon allowing the thus-assembled parts to cool, a slight residual circumferential tension (clamping) will develop in haptic 66 to permanently retain the assembled relationship.

The preferred material for lens element 10' is optical glass, of selected index of refraction as previously noted. And in that event, the rabbet 65 is preferably the result of suitably masked chemical etching, the etching proceeding axially from one to the exclusion of the other axial end of the lens element; as shown, the rabbet and the rabbet-forming etch involve only the convex end of the lens element. A suitable etchant is hydrofluoric acid, diluted to about 20 percent in water.

Figure 13:
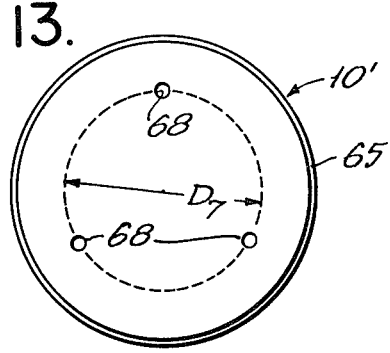
FIGS. 13, 14 and 15 are similar end views to show illustratively varied formations in the lens element of FIGS. 11 and 12.
Figure 14:
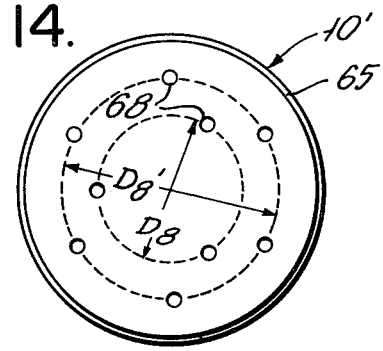

It is a feature of the invention that the lens element 10', although much smaller than those in current contact-lens use, shall be characterized by spaced through-passages, such as passages 68 in FIG. 13, for permitting air access to a corresponding plurality of lens-covered regions of the cornea. As shown, in FIG. 13, three such passages are provided, at equal spacing from each other and on a single common geometrical circle of diameter $D_7$ about the central optical axis. In FIG. 14, such passages are shown equally spaced on each of two concentric circles of diameters $D_8$–$D_8'$ about the axis, and is FIG. 15, the $D_9$ diameter circle of such passages surrounds a central passage 68' of the same character.

Figure 15:
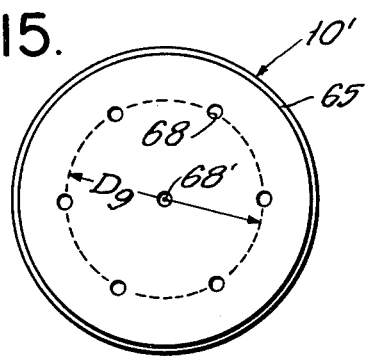

The passages 68–68' of FIGS. 13 to 15 may suitably be of 0.25 to 0.5 mm diameter and the geometrical circle diameters may be in the range of 4 to 8 mm, depending on the number and distribution of the passages and the peripheral diameter $D_6$ of the lens element. In any case, however, the combined sectional area of all such passages is preferably less than one per cent of the peripherally included area of the lens, so that "breathing" is possible without degrading vision.

Figure 16:
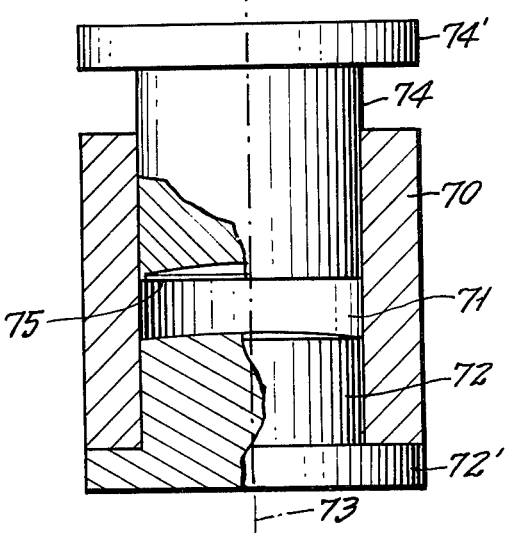
FIG. 16 is a simplified view in elevation, partly broken away and in longitudinal section, to show a compression-die configuration to produce contact-lens structure of FIG. 12.

While it is possible and highly satisfactory to provide ground optically finished front and back surfaces for a glass lens element 10', this is a relatively expensive technique. My current preference is to use compression dies on a heat-softened blank to form the desired convex and concave surfaces of the lens. Such apparatus is shown, simplified, in FIG. 16. Basically, an annular body 70 provides a straight cylindrical bore 71 of diameter to clear and locate an inserted blank for element 10'. Bore 71 receives a bottom-inserted fixed-die element 72 having an upper convex spherical surface of radius $R_1$ on a central axis 73; at its other end, bore 71 provides axial guidance for a movable-die element 74 having a lower concave spherical surface of radius $R_2$, also on the central axis. Assuming the prior etching of rabbet 65, a heat-softened flat glass blank for element 10' is inserted in bore 71 (rabbeted side up) so that upon descent of the upper die element 74, the projected rim 75 at the periphery of the concave end of element 74 will locate in the rabbet 65 upon initial contact with element 10'. Thereafter, compression of die elements 74-72 squeezes the softened glass blank into its ultimate desired curvatures, dependent of course upon the curvatures associated with the respective convex and concave forming surfaces of the die elements.

What has been described thus far applies to the manufacture of lens elements 10' in which no astigmatic correction is prescribed, namely, meniscus-lens elements in which $R_1$ and $R_2$ are centered on the optical axis of the element 10'. To provide for astigmatic correction, it is merely necessary that for one of the die elements 72 or 74, the curvature-forming spherical surface thereof shall be based on a center that is offset from the optical axis (i.e., eccentric with respect to the center of the other die-element spherical surface), the extent of the offset being of course a function of the prescription statement of degree of correction required. In the event of such eccentric offset, it is convenient to externally indicate the angular direction of the offset, as by appropriate edge marking on the flange 72' (or 74') of the die element 72 (or 74) having the eccentric offset of its spherical center.

The haptic 66 is also preferably etch-cut from thin flat sheet glass stock, and is therefore initially as shown in FIG. 11. According to one method of assembly, such a glass haptic blank is heat-softened and compression-die formed into dished spherical shape in conformance with cornea curvature, prior to its assembly to the inserted lens element 10'; such forming is exemplified in FIG. 12, being shown after completion of its above-described assembly. It will be understood that the chemical etching by means of which the haptic blank is cut from sheet stock may also provide fenestration as desired in the haptic blank. Such fenestration may take one of the forms described in connection with FIGS. 1 to 9, or it may be otherwise as desired, for example, foraminated with spaced apertures as described at 68 for lens element 10'.

It is also desirable that either the etched design or the die-forming design operative upon the haptic 66 shall provide a built-in recognizable angular reference identification (indicium) so that the ultimate user can always apply his lens assembly in consistently correct angular orientation; such a die-formed indicium appears at 79 in FIG. 12. Recognizable orientation is particularly important when the lens element 10' incorporates astigmatism correction, and it will be understood that the angle identification mentioned above in connection with eccentric offset in the die-element relation must be correctly positioned with respect to the haptic reference identification (indicium), upon haptic to lens element assembly, the correct angular relation being as prescribed for the ultimate user's eye.

The described embodiments of the invention will be seen to achieve all stated objects. Importantly, the invention brings light weight and substantially reduced bulk and surface area to the contact-lens art, plus the inherent capability of providing optically finished glass lens elements, with astigmatic correction, if needed; further, photochromic glass at 10 provides a hitherto unavailable feature in a contact lens configuration. Fenestration areas are substantial, radially outside the supported lens element 10, being preferably at least four times the end area of the lens element, such area being taken as within effective perimeter limits of the geometric circular or oval (elliptical) contour to which the foot formations are tangent. Except for the "opaque" annulus 41 (41') of FIGS. 8 and 8A, all other haptic regions and materials are preferably clear and transparent, foot formations of such haptic regions being effectively invisible to the eye of an observer.

Not only does the invention bring above-noted benefits of optically finished glass to the contact-lens art, but an important safety factor is also provided. In embodiments involving plastic-sheet haptics, the plastic sheets of the haptic fully enclose and support the lens element in at least the region of its rim; in other words, it is at least the most delicate and fracturable part of the lens which is protected by such plastic-sheet enclosure. In glass-haptic situations as described in connection with FIGS. 10 and 10A, the haptic sheet 60, being bonded to lens element 10 over its full area, provides reinforcement to the otherwise more fracturable rim region of the lens element 10; in the event that lens element 10 is a meniscus lens, the haptic sheet 60 is preferably centrally open to the diameter $D_3$ (see FIG. 5), but there will be an annular overlap ($D_1$ minus $D_3$) within which sheet 60 and lens 10 are bonded, thus providing lens-rim reinforcement, in addition to the described support and positioning functions of the haptic. And in the etched-glass situations discussed in connection with FIGS. 11 to 15, it will be noted that as a result of chemical etching there is no chipping, nicking or the like degradation of remaining glass, as at the rabbeted periphery, so that inherent strength and resistance to shatter are preserved in the etched glass components.

It should be further observed that although curvatures and diopter ranges have been mentioned by way of illustration, these ranges are in no sense by way of limiting the invention. For example, the invention will be seen to have application to aphakic patients, i.e., to those whose cataracted natural lens has been surgically removed but for whom an external lens, rather than an implanted intraocular lens, has been prescribed. Such lenses may be of the structure, nature and combinations herein described, but with a stronger finished optical element 10, e.g., having power in the order of 10 or more diopters. When such stronger lenses are of glass, the thickness of the lens element 10 per se will still be very much less than for a conventional contact lens prescribed for the same situation.

While the invention has been described in detail for preferred forms shown, it will be understood that modifications may be made without departure from the claimed scope of the invention. For example, the technique of retaining an optical element by and between laminated plastic sheets which become the haptic lends itself to intraocular-lens application, so that for example, a configuration as in FIG. 7, and with three or more foot formations within an outer circular locus of 12 to 14 mm diameter may serve well for anterior-chamber implantation, relying upon the foot formations to develop stabilizing support at the scleral ridge (adjacent the base of the iris). Of course, in that event, the haptic sheets should provide a more stiff radial-support action, in that they stand without contact analogous to the described cornea-adherent extraocular applications herein; thus, for intraocular application the overall haptic thickness $T_1$ is preferably about 10 mils, and of course lens curvatures will be of shorter radius in view of the vitreous-humor environment in which such lenses must function.

What is claimed is:

1. A contact lens assembly adapted for removable mounting to the cornea of an eye, comprising an optically finished lens element having a circular periphery characterized by a convex outer surface having a circumferentially continuous peripheral-edge rabbet formation in the outer-surface side of said element, and a single-piece haptic of flexible sheet material having a central circular opening at the rim of which said haptic has circumferentially continuous seated engagement with said rabbet formation and thereby mounts said lens element, said haptic being so axially compliant as to conform to the curvature of the cornea and to be self-adherent thereto via surface moisture of the cornea, whereby the self-adherent force upon haptic contact with the cornea is operative at the periphery of said lens element to axially inwardly retain the inner surface of the lens element in contact with the cornea.

2. The lens assembly of claim 1, in which said lens element is of optical glass.

3. The lens assembly of claim 1, in which said haptic means is of plastic material.

4. The lens assembly of claim 1, in which said haptic means is of glass.

5. The lens assembly of claim 1, in which said lens element is characterized by spaced longitudinally open passages.

6. The lens assembly of claim 5, in which said passages are of diameter substantially in the range 0.25 to 0.5 mm.

7. The lens assembly of claim 5, in which said haptic means is characterized by a plurality of spaced longitudinally open passages.

8. The lens assembly of claim 6, in which the number of passages is three or more having a combined effective sectional area which is less than one percent of the peripherally included area of said lens element.

9. The lens assembly of claim 8, in which a plurality of said passages are at equal angular spacing on a geometric circle about the optical axis of said lens element, the spacing between adjacent passages of said plurality being at least to the magnitude of the radius of the geometric circle.

10. The lens assembly of claim 5, in which one of said passages is on the optical axis of the lens element, a plurality of said passages being angularly spaced on a geometric circle about said axis.

11. The lens assembly of claim 2, in which said rabbet formation is the product of chemical etching.

12. The lens assembly of claim 5, in which said lens element is of optical glass and said passages are the product of chemical etching.

13. The lens assembly of claim 12, in which said rabbet formation is the product of chemical etching concurrent with the etching of said passages.

14. The lens assembly of claim 1, in which said haptic is substantially fenestrated in its operative area external to the central circular opening thereof.

15. A contact-lens assembly adapted for removable mounting to the cornea of an eye, comprising meniscus-lens means of optical glass, said lens means having a convex outer surface and a concave inner surface and having a circular periphery characterized by a circumferentially continuous peripheral-edge rabbet formation in the outer-surface side of said lens means, and a single-piece annular haptic of sheet material having a circular opening at the rim of which said haptic means has circumferentially continuous seated engagement with said rabbet formation and thereby mounts said lens means, said haptic means having generally spherically dished convex and concave surface at its respective axial ends, the convex surfaces of said haptic means and of said lens means being at the same axial end of said assembly, and said haptic being so axially compliant as to conform to the curvature of the cornea and to be self-adherent thereto via surface moisture of the cornea, whereby the self-adherent force upon haptic contact with the cornea is operative at the periphery of said lens element to axially inwardly retain the inner surface of the lens element in contact with the cornea.

16. The lens assembly of claim 15, in which said haptic means is of glass.

17. The lens assembly of claim 15, in which said haptic means if of plastic.

18. The lens assembly of claim 16, in which said haptic means is in circumferentially tensed engagement with said rabbet formation.

19. The contact-lens assembly of claim 15, in which the center of curvature of one of the meniscus-lens surface is eccentric to the center of curvature of the other meniscus-lens surface, whereby said lens means has an inherent astigmatism-corrective property, and in which said haptic is characterized by a visually observable indicium of a reference location at one angular location about the circle of said opening, said lens means and said haptic means being assembled in angularly oriented relation such that the astigmatism-correction axis bears a particular angular relation to said reference location, said oriented relation being determined by prescription appropriate to the astigmatic condition of the eye to be fitted.

20. The method of making a two-piece contact-lens assembly, wherein a circular lens element having a circumferentially continuous peripheral-edge rabbet with land and shoulder surfaces in the outer-surface side is engaged at the rabbet to the circular rim of a centrally apertured flexible haptic element of heat-expandible sheet material, which method comprises heating said haptic element to expand the rim circumference of its circular aperture, such expansion being to a degree to permit axial insertion of the rabbet land surface to be engaged, making such insertion to the point of axial location at the shoulder surface of the rabbet formation, and retaining the thus-assembled relation while allowing the haptic element to cool and thus shrink into tensed engagement with said land surface.

21. The method of claim 20, wherein both the lens element and the haptic element are of glass.

22. The method of making a glass contact-lens element of meniscus configuration and adapted for assembly to a mounting haptic, which method comprises selecting a thin sheet of optical glass of desired refractive index, chemically etching a circular line to define and separate a lens blank from said sheet, selecting a pair of die elements having cooperating convex and concave surface curvatures appropriate to desired ultimate meniscus-lens curvatures, heating the lens blank to softened condition, forming meniscus curvatures by axially compressing the softened blank between said die elements, and allowing the die-formed blank to cool.

23. The method of claim 22, in which the center of curvature of one of said die elements is eccentric to the axis of die compression, whereby the die-formed blank has an inherent astigmatism-corrective property.

24. A glass contact-lens element having a circular periphery characterized by a convex outer surface having a circumferentially continuous peripheral-edge rabbet formation in the outer-surface side of said element, said rabbet formation being adapted to mount to the central aperture of suitable axially compliant haptic structure, said glass element being characterized by spaced longitudinally open passages of combined effective sectional area which is less than one percent of the peripherally included area of said lens element.

25. The lens element of claim 24, in which said rabbet formation and passages are the product of concurrent masked chemical etching from both axial ends of said lens element, the mask on the axial end which includes said convex surface being peripherally open to enable rabbet and passage etching from one end, the mask on the other axial end being peripherally closed to prevent rabbet formation at said other end, and both masks having passage-defining openings which are in longitudinal register to permit concurrent passage formation from both axial ends.

26. The method of making a glass contact-lens element having a convex outer surface and a circular periphery characterized by a peripheral-edge rabbet formation in the axial end which includes said outer surface, which comprises selecting a thin sheet of optical glass of desired refractive index, cutting a circular blank from said sheet by chemically etching a circular border line to characterize the blank with said circular periphery, chemically etching said rabbet formation from said axial end, chemically etching in said blank a plurality of spaced longitudinally open passages of combined effective sectional area which is less than one percent of the peripherally included area of said lens element, said blank being softened by heat, and front and back lens surfaces being compressionally formed on the softened blank.

27. The method of claim 26, wherein the heating and compressive forming steps are performed after the etching steps.

28. The method of claim 26, wherein the heating and compressive forming steps are performed before the etching steps.

29. The method of making a two-piece glass contact-lens assembly wherein a glass contact-lens element of meniscus configuration is assembled to a dished glass haptic element, which method comprises selecting a thin sheet of optical glass of desired refractive index, chemically etching a circular line to define and separate a lens blank from said sheet, said etching step including the etched formation of a circular rabbeted edge of the side of the lens blank which is to become the convex side of the lens element, selecting a thin sheet of glass and etching the same to define a blank for the haptic element, assembling both blanks to ultimate co-axial relation with the haptic blank seated at the rabbeted edge of the lens blank, selecting die elements having cooperating convex and concave surface curvatures appropriate to desired ultimate meniscus-lens curvatures and to desired ultimate dished haptic curvature, heating the assembled blanks to softened condition, concurrently forming the meniscus curvatures and the haptic curvature by axially compressing the softened blanks between said die elements, and allowing the die-formed assembled blanks to cool, the thickness of said haptic glass sheet being so thin and bendably compliant that the haptic resulting from die compression is sufficiently axially compliant to conform to the curvature of the cornea and to be self-adherent thereto via surface moisture of the cornea.

30. The method of claim 29, in which the haptic-forming concave die surface has an indicium-forming discontinuity at one angular reference-defining location.

31. The method of claim 30, in which the center of curvature of the lens-defining surface of one of said die elements is eccentric to the axis of die compression, the angular location of such eccentricity being so selected in relation to the angular location of said indicium-forming discontinuity that the astigmatism-correction axis of a die-formed lens and haptic assembly is characterized by a prescribed angle, referenced to the indicium and appropriate to the astigmatic condition of the eye to be fitted.

* * * * *